United States Patent [19]
Lee et al.

[11] Patent Number: 4,808,208
[45] Date of Patent: Feb. 28, 1989

[54] PHENOLIC SAFENERS FOR GLYPHOSATE HERBICIDES

[75] Inventors: Tsung T. Lee; Alvin N. Starratt, both of London, Canada

[73] Assignee: Canadian Patents & Development Ltd., Ottawa, Canada

[21] Appl. No.: 78,709

[22] Filed: Jul. 28, 1987

[30] Foreign Application Priority Data

Aug. 4, 1986 [GB] United Kingdom ............... 8618992

[51] Int. Cl.[4] .................. A01N 57/20; A01N 37/38
[52] U.S. Cl. ........................................ 71/86; 71/115
[58] Field of Search .................................. 71/115, 86

[56] References Cited

U.S. PATENT DOCUMENTS 3,131,509  5/1964  Hoffman ........................ 71/103
3,799,758  3/1974  Franz ............................. 71/86
4,392,884  7/1983  Pallos et al. ................... 71/118

Primary Examiner—Richard L. Raymond
Assistant Examiner—Susan P. Treanor
Attorney, Agent, or Firm—Alan A. Thomson

[57] ABSTRACT

Glyphosate herbicides are used for weed control in crops. It has been found that the desired crop plants can be protected from the herbicidal effect by providing a pretreatment so that the crop plants have assimilated a phenolic compound found to give a safening effect.

8 Claims, No Drawings

PHENOLIC SAFENERS FOR GLYPHOSATE HERBICIDES

This invention is directed to providing protection for crop plants so that the crop plants are able to tolerate herbicide treatments used for weed control. Selected phenolic compounds have been found to protect crop plants from the glyphosate herbicides.

The use of phenolic safeners for glyphosate is a potential alternative to genetic engineering approaches to develop crop plants resistant to glyphosate (see Chemical and Engineering News, pp. 4 and 5, Nov. 11, 1985).

From available information, the inhibition of 5-enolpyruvylshikimate-3-phosphate synthase (EC 2.5.1.19) in the shikimate pathway is the primary site of action of the herbicide glyphosate [N-(phosphonomethyl)glycine] in plants (11). As expected, since the shikimate pathway is the major route for the biosynthesis of aromatic amino acids and phenolic compounds, the direct consequence of the inhibition has been shown to be decreased protein and phenolic levels (1-4). Glyphosate also affects other biochemical processes, such as those leading to a decrease in free indole-3-acetic acid (IAA) levels (6), which are important to plant growth. A causal relationship between the level of free IAA and plant growth as affected by glyphosate has been indicated by a promotion of lateral shoot growth by sublethal concentrations of glyphosate (8) and a partial reversal of glyphosate inhibition of growth by auxin in tobacco and soybean tissue culture systems (5,6). The decrease in the free IAA level by glyphosate has been attributed to the enhanced rate of IAA metabolism (6,7). Moreover, since many phenolic compounds are inhibitors of IAA oxidation (10), a minor route of IAA metabolism, it has been proposed that the inhibition of biosynthesis of phenolic compounds by glyphosate may be related to the increased metabolism of IAA. More important, however, we have recently found that the phenol, 2,6-dihydroxyacetophenone, is a potent inhibitor of conjugation of IAA with L-aspartic and L-glutamic acids (9), a major route for IAA metabolism in certain plant species. The experiments reported here further demonstrate that selected phenolic compounds can prevent the metabolism of IAA especially via the conjugative route and, as a consequence, reverse the inhibition of growth observed for glyphosate-treated plants.

SUMMARY OF THE INVENTION

This invention includes a method of protecting desired crop plants from the effect of glyphosate herbicides used for weed control, comprising providing that the crop plants have assimilated safening amounts of a phenolic compound selected to have a protective effect against glyphosate herbicides, in advance of application of glyphosate herbicides.

The application and subsequent assimilation of phenolic safener can be achieved by at least one of
(a) seed treatment before germination,
(b) localized soil treatment, and
(c) crop plant or seedling treatment.

The crop seeds may be coated with the selected phenolic compound in any suitable coating formulation. The soil may be treated (or pre-treated before seeding) with the phenolic compound to permit uptake through the roots. Spraying the crop plants with an aqueous solution of the phenol (or other suitable carrier formulation) at an appropriate interval in advance of herbicide applications, is effective also.

A kit for weed control in crops comprises glyphosate herbicide and the selected phenolic compound is separate containers.

Preferably the phenolic safener is selected from compounds of the formula:

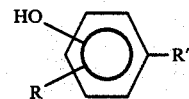

where
R=H, OH or OCH$_3$, and

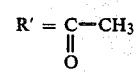

or CH=CH—COOH.

DETAILED DESCRIPTION

The herbicides are of the glyphosate type having the N-(phosphonomethyl)glycine moiety present. This type is described extensively in the literature, including U.S. Pat. Nos. 3,799,758 and 4,341,549. Certain of these herbicides are available under the trademark "Roundup".

Chemical specificity

The initial selection of the phenolic compounds for testing protection of plants from glyphosate-induced inhibition of growth was based on two kinds of in vitro studies: (1) plant callus bioassay for assessing effect on growth, (2) radiobiochemical assay for assessing effect on metabolism of the plant hormone IAA. The results (see Examples below) obtained from the soybean callus bioassay clearly indicate a structural specificity for the growth-regulating activity of 2,6-dihydroxyacetophenone in this plant (Table 7). In the radiobiochemical assay, a chemical specificity has also been demonstrated for the regulatory activity of 2,6-dihydroxyacetophenone on IAA metabolism (Table 8). In buckwheat seedlings, however, three other phenolic compounds were equally or more active than 2,6-dihydroxyacetophenone (Table 9). Similarly, with the soybean seedlings ferulic acid and caffeic acid were equally or more effective than 2,6-dihydroxyacetophenone. These data together with those in Tables 3a and 3b and others suggest that there is a structural requirement of phenols but the specificity may vary with plant species. The compounds identified to date as being preferred for providing protection from glyphosate may be represented by the following generalized formula:

where
R=H, OH or OCH$_3$, and

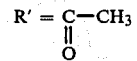

or CH=CH—COOH.

Suitable compounds include coumaric acid, ferulic acid, caffeic acid as well as 2,6-dihydroxyacetophenone.

This is based on limited tests so a much larger number of phenols needs to be examined to more precisely describe structure-activity relationships. A series of phenolic compounds and concentrations should be tested for each crop plant in conjunction with different glyphosate concentrations before an optimized application program can be devised for a specific crop.

Methods of application

A number of applications are envisioned. (1) Phenolic safeners could be applied as a seed coating thereby providing selective protection of the crop from the effects of glyphosate. A recent article in Span (29(2): 54–56, 1986) discusses the application of crop protection chemicals by seed treatment. Seeds could be treated with powder or film-coated with the phenol safeners mixed with appropriate diluters. Water would serve as the preferred solvent for film application. For powder application, inert solid extenders, such as natural clays, diatomaceous earth and synthetic minerals such as those derived from silica, may be employed; (2) pretreatment of transplants by phenolic safeners may permit them to be set in fields freshly or subsequently treated with glyphosate; (3) such compounds may be applied in conjunction with trickle irrigation systems which would permit selective application to crop plants; (4) phenolic safeners may be applied as a row spray, using water-based formulations to which it would be beneficial to add a wetting agent; (5) crop plants could be pretreated with phenolic safeners before attempts are made to selectively apply glyphosate. This would apply both within the field and in adjacent areas where herbicide drift is a problem.

The amount of phenolic safener may be any amount found effective to decrease the herbicidal effect on desired crop plants and allow their growth and crop production. Typical amounts are illustrated in the examples below.

The interval between phenolic safener application and herbicide application may vary widely as long as the phenolic compound is present in the plant tissue to exert its safening effect. It appears that this interval may range from about 1 day up to 1 week or more.

Because the protection is based on the basic principle of preventing glyphosate interference with IAA metabolism and this natural hormone occurs universally in the plant kingdom, it is believed that a variety of crop plants could be protected similarly.

The following examples are illustrative and supportive.

EXAMPLE 1

Plant tissue culture tests were carried out on growing soybean and tobacco callus cultures. The fresh weight of standard inoculants of callus 21 days after adding glyphosate to 1 mM or 20 μM concentration in the medium, with and without a concurrent treatment (same day as glyphosate addition) with 2,6-dihydroxyacetophenone to 0.5 mM or 0.1 mM concentration in the medium, was measured compared to a control (no additions). The results, given in Tables 1 and 2, indicate that this phenol protected the plant tissues from glyphosate at the concentrations tested.

Results obtained from further soybean callus bioassays (see Table 7) indicate a structural specificity for the growth-regulating activity of phenols at least in soybean callus.

EXAMPLE 2

Four phenolic compounds (as 0.5 mM aqueous solutions) were sprayed on buckwheat seedlings one day in advance of spraying with a 0.1 mM solution of glyphosate. The plant heights were measured 10 days after the glyphosate spray. The results of two test series are given in Tables 3a and 3b. The phenolic compounds protected the plants to a varied degree.

Three of the phenolic compounds were tested similarly on *Teucrium canadense* plants and the results are given in Table 4. These latter 3 phenolic compounds were less effective in *T. canadense* plants than in buckwheat.

EXAMPLE 3

The effect of a prior soil drench of selected phenolic compound 2 or 3 days preceding the glyphosate spray is given in Table 5. The soil drench was by addition of 200 ml of a 0.1 mM solution to 15 cm diameter pots. The observed effect is similar to spraying the plants.

Results such as in Tables 6 and 10 have indicated that the phenol must be applied as a pretreatment rather than as a concurrent or post-treatment.

EXAMPLE 4

Tests were carried out on the effect of phenolic compounds on the metabolism of carbon-14 labelled indole acetic acid in two plant species. For the short-term experiments with [2-$^{14}$C] IAA (Amersham), the plants, which were sprayed with deionized water or 0.2 mM glyphosate once 6 days earlier, were cut near the soil surface and kept in the dark for 12 h with the cut-end immersed in deionized water or 2 mM 2,6-dihydroxyacetophenone. After the pretreatment, the stems were cut into 5 mm segments, fed with [2-$^{14}$C] IAA and analyzed.

In these radiobiochemical assays, a chemical specificity among the phenolic compounds and among the plant species is evident. (See Tables 8 and 9.)

EXAMPLE 5

Three-week-old plants of American germander (*Teucrium canadense L.*) were used for the experiments. They were germinated in soil from 1-bud segments of the rhizomes and grown in an environmental-controlled chamber at 25° C. under 12 h light and 12 h dark cycles. The light (270 μE/M$^2$/sec) was provided by a mixture of incandescent and fluorescent lamps. The experiments were started with a pre-treatment of the plants with a 0.5 mM aqueous solution of 2,6-dihydroxyacetophenone. The pretreatment was applied either by spraying the plants to wet the upper surfaces of all leaves or by adding 200 ml to the soil contained in 15 cm pots. On the same day or one to 3 days later the plants were sprayed as above with 0.2 mM glyphosate prepared by mixing appropriate volumes of Roundup (trademark—Monsanto) with deionized water. The control plants were treated with deionized water only. Ten days after glyphosate application, the height of each plant was measured. Each treatment had 1530 plants and each experiment was repeated twice. Results are given in Table 10. These results indicate that pretreatment with the phenol by foliar spray or by feeding through roots protected the plants from glyphosate inhibition of growth.

EXAMPLE 6

Two-week-old soybean seedlings were pretreated with 0.5 mM aqueous solution of ferulic acid, caffeic acid or 2,6-dihydroxyacetophenone by soil drench or foliar spray, or both, 1-3 days preceding the glyphosate spray. The pretreatment reduced the inhibitory effect of glyphosate on growth. Ferulic acid or caffeic acid was equally or more active than 2,6-dihydroxyacetophenone. Two other phenols, chlorogenic acid and scopoletin, were less effective. The results are given in Tables 11-15.

TABLE 1

Reversal of glyphosate-induced inhibition of fresh weight growth by 2,6-dihydroxyacetophenone in soybean callus bioassay.

| Treatment | Callus Fresh weight* (g/flask) |
|---|---|
| Control | 7.7 |
| Glyphosate (1 mM)** | 5.4 |
| Glyphosate (1 mM)** + 2,6-dihydroxyacetophenone (0.5 mM)** | 7.6 |

*Mean values of 5 experiments recorded 3-4 weeks after inoculation
**Concentration in agar medium at inoculation

TABLE 2

Reversal of glyphosate-induced inhibition of fresh weight growth by 2,6-dihydroxyacetophenone in tobacco callus bioassay.

| Treatment | Callus Fresh weight* (g/flask) |
|---|---|
| Control | 6.0 |
| Glyphosate (20 μM) | 2.2 |
| Glyphosate (20 μM) + 2,6-dihydroxyacetophenone (0.1 mM) | 5.3 |

*Mean values of 2 experiments recorded 5 weeks after inoculation

TABLE 3a

Effects of phenolic compounds as a pretreatment on glyphosate-induced inhibition of elongative growth of buckwheat seedlings.

| Pretreatment (spray one day before glyphosate) | Glyphosate spray | plant height* (cm) |
|---|---|---|
| Water | 0 | 21.4 |
| Water | 0.1 mM | 9.3 |
| 2,6-dihydroxyacetophenone (0.5 mM) | 0.1 mM | 14.5 |
| p-Coumaric acid (0.5 mM) | 0.1 mM | 14.1 |
| Caffeic acid (0.5 mM) | 0.1 mM | 16.5 |
| Ferulic acid (0.5 mM) | 0.1 mM | 16.4 |

*Mean values of 4 experiments recorded 9-12 days after glyphosate spray

TABLE 3b

Effects of phenolic compounds other than 2,6-dihydroxyacetophenone on glyphosate-induced inhibition of elongative growth of buckwheat seedlings.

| Pretreatment (spray one day before glyphosate) | Glyphosate spray | plant height* (cm) |
|---|---|---|
| Water | — | 18.9 |
| Water | 0.1 mM | 10.5 |
| p-Coumaric acid (0.5 mM) | 0.1 mM | 20.2 |
| Caffeic acid (0.5 mM) | 0.1 mM | 20.5 |
| Ferulic acid (0.5 mM) | 0.1 mM | 21.0 |

*Measurements recorded 10 days after glyphosate spray

TABLE 4

Effects of phenolic compounds other than 2,6-dihydroxyacetophenone on glyphosate-induced inhibition of elongative growth of *Teucrium canadense* plants.

| Pretreatment | Glyphosate spray | plant height* (cm) |
|---|---|---|
| Water | — | 23.2 |
| Water | 0.2 mM | 13.0 |
| p-Coumaric acid (0.5 mM) | 0.2 mM | 10.2 |
| Caffeic acid (0.5 mM) | 0.2 mM | 14.4 |
| Ferulic acid (0.5 mM) | 0.2 mM | 14.9 |

*Measurements recorded 8 days after glyphosate spray.

TABLE 5

Effect of 2,6-dihydroxyacetophenone used as a prior soil drench on glyphosate-induced inhibition of elongative growth of *Teucrium canadense* plants.

| Pretreatment | Glyphosate spray | plant height* (cm) |
|---|---|---|
| Water | — | 18.6 |
| Water | 0.2 mM | 10.1 |
| 2,6-Dihydroxyacetophenone used 2 days earlier | 0.2 mM | 22.4 |
| 2,6-Dihydroxyacetophenone used 3 days earlier | 0.2 mM | 21.3 |

*Measurements recorded 10 days after glyphosate spray.

TABLE 6

Effect of 2,6-dihydroxyacetopheone as a post or pretreatment on glyphosate-induced inhibition of elongative growth of *Teucrium canadense* plants.

| Pretreatment (spray) | Glyphosate spray | plant height* (cm) |
|---|---|---|
| Water | — | 26.5 |
| Water | 0.2 mM | 16.7 |
| 2,6-Dihydroxyacetophenone as pretreatment | 0.2 mM | 21.9 |
| 2,6-Dihydroxyacetophenone as post treatment | 0.2 mM | 16.0 |

*Measurements recorded 10 days after glyphosate spray.

TABLE 7

A comparison of the effects of 2,6-dihydroxyacetophenone and structurally related compounds on fresh weight growth in soybean callus bioassay.

| Compound Added at Inoculation (to 0.5 mM Concentration) | Fresh weight yield* (% of control) |
|---|---|
| 2,6-Dihydroxyacetophenone | 136 |
| 2,5-Dihydroxyacetophenone | 94 |
| 2,4-Dihydroxyacetophenone | 81 |
| 3,4-Dihydroxyacetophenone | 102 |
| Resorcinol | 100 |
| 2-Methylresorcinol | 103 |
| 2,6-Dihydroxybenzoic acid | 43 |
| 2,6-Dihydroxybenzoic acid methyl ester | 44 |
| 2,6-Dihydroxyacetophenone oxime | 113 |
| 3-Bromo-2,6-dihydroxyacetophenone | 125 |
| 2-Hydroxyacetophenone | 44 |
| 2-Hydroxy-3-methoxyacetophenone | 99 |
| 2-Hydroxy-4,6-dimethylacetophenone | 59 |
| 2,4,6-Trihydroxyacetophenone | 113 |
| β-Tubanol | 80 |
| p-Coumaric acid | 88 |
| Caffeic acid | 104 |
| Ferulic acid | 103 |

*Mean values of 1-12 (mostly 3) experiments recorded 3-4 weeks after inoculation.

TABLE 8

A comparison of the effects of 2,6-dihydroxyacetophenone and structurally related compounds on metabolism of IAA in *Teucrium canadense* plants.

| Compound | [2-$^{14}$C]IAA metabolized (% of total uptake) |
|---|---|
| Water | 83.6 |
| 2,6-Dihydroxyacetophenone | 28.0 |
| 2,5-Dihydroxyacetophenone | 90.1 |
| 3,4-Dihydroxyacetophenone | 79.8 |
| 2,4,6-Trihydroxyacetophenone | 81.0 |

TABLE 9

Effects of phenolic compounds used as a pretreatment on glyphosate-induced decrease of free IAA level in buckwheat seedlings.

| Pretreatment | Glyphosate spray | Free [2-$^{14}$C]IAA level (% of total uptake) |
|---|---|---|
| Water | — | 42.4 |
| Water | 0.1 mM | 27.8 |
| 2,6-dihydroxyacetophenone | 0.1 mM | 31.5 |
| p-Coumaric acid | 0.1 mM | 30.9 |
| Caffeic acid | 0.1 mM | 32.7 |
| Ferulic acid | 0.1 mM | 35.8 |

TABLE 10

Effect of 2,6-dihydroxyacetophenone on glyphosate inhibition of growth of *Teucrium canadense* plants.

| Treatment | Plant Height* (cm) |
|---|---|
| Water (control) | 34.5 |
| 2,6-Dihydroxyacetophenone added to soil 3 days before glyphosate (0.2 mM) spray | 33.9 |
| 2,6-dihydroxyacetophenone added to soil 1 day before glyphosate spray | 31.7 |
| 2,6-dihydroxyacetophenone added to soil the same day as glyphosate spray | 23.4 |
| 2,6-dihydroxyacetophenone sprayed on plants 1 day before glyphosate spray | 30.3 |
| Glyphosate spray only | 19.4 |

*Measurements recorded 10 days after glyphosate spray.

TABLE 11

Effect of phenolic compounds as a pretreatment on glyphosate-induced inhibition of elongative growth of soybean seedlings.

| Pretreatment* | Glyphosate Spray | Plant height** (cm) |
|---|---|---|
| Water | 0 | 40.8 |
| Water | 0.1 mM | 19.0 |
| 2,6-Dihydroxyacetophenone | 0.1 mM | 28.6 |
| Ferulic acid | 0.1 mM | 28.6 |

*0.5 mM aqueous solutions of the phenolic compounds were added to soil and sprayed to plants 3 days before glyphosate spray.
**Measurement recorded 12 days after glyphosate spray.

TABLE 12

Effect of phenolic compounds as a pretreatment on glyphosate-induced inhibition of elongative growth of soybean seedlings.

| Pretreatment* | Glyphosate Spray | Plant height** (cm) |
|---|---|---|
| Water | 0 | 36.9 |
| Water | 0.1 mM | 25.6 |
| 2,6-Dihydroxyacetophenone | 0.1 mM | 28.5 |
| Ferulic acid | 0.1 mM | 35.8 |
| Caffeic acid | 0.1 mM | 34.8 |

*0.5 mM aqueous solutions of the phenolic compounds were sprayed to seedlings 2 days before glyphosate spray.
**measurements recorded 10 days after glyphosate spray.

TABLE 13

Effect of ferulic acid as a pretreatment on glyphosate-induced inhibition of elongative growth of soybean seedlings.

| Pretreatment* | Glyphosate Spray | Plant height** (cm) |
|---|---|---|
| Water | 0 | 25.1 |
| Water | 0.1 mM | 11.0 |
| Ferulic acid | 0.1 mM | 22.2 |

*0.5 mM aqueous solution of ferulic acid was added to soil and sprayed 2 days before glyphosate spray.
**Measurement recorded 12 days after glyphosate spray.

TABLE 14

Effect of phenolic compounds as a pretreatment on glyphosate-induced inhibition of elongative growth of soybean seedlings.

| Pretreatment* | Glyphosate Spray | Plant height** (cm) | Fresh weight** (g/plant) |
|---|---|---|---|
| Water | 0 | 36.8 | 7.7 |
| Water | 0.1 mM | 23.7 | 4.4 |
| 2,6-Dihydroxyacetophenone | 0.1 mM | 30.6 | 6.0 |
| Ferulic acid | 0.1 mM | 32.7 | 6.7 |
| Caffeic acid | 0.1 mM | 32.2 | 6.3 |

*0.5 mM aqueous solutions of the phenolic compounds were added to soil and sprayed to plants 3 days before glyphosate spray.
** Measurements recorded 13 days after glyphosate spray.

TABLE 15

Effect of phenolic compounds as a pretreatment on glyphosate-induced inhibition of elongative growth in soybean seedlings.

| Pretreatment* | Glyphosate Spray | Plant height** (cm) | Fresh weight** (g/plant) |
|---|---|---|---|
| Water | 0 | 27.5 | 4.0 |
| Water | 0.1 mM | 12.8 | 2.4 |
| Chlorogenic acid | 0.1 mM | 18.5 | 3.4 |
| Scopoletin | 0.1 mM | 17.8 | 3.1 |

*0.5 mM aqueous solution of the phenolic compounds was added to soil and sprayed to plants 3 days before glyphosate spray.
**Measurements recorded 8 days after glyphosate spray.

BIBLIOGRAPHY (1) Cole, D. J., Dodge, A. D. and Caseley, J. C. 1980. Some biochemical effects of glyphosate on plant meristems. J. Exp. Bot. 31: 1665–1674.

(2) Duke, S. O. and Hoagland, R. E. 1985. Effects of glyphosate on metabolism of phenolic compounds. In Grossbard, E. and Atkinson, D. (eds.), "The herbicide glyphosate". pp. 75–91. Butterworths, London.

(3) Hollander, H. and Amrhein, N. 1980. The site of the inhibition of the shikimate pathway by glyphosate. I. Inhibition by glyphosate of phenylpropanoid synthesis in buckwheat (*Fagopyrum esculentum* Moench). Plant Physiol. 66: 823–829.

(4) Ishikuru, N. and Takeshima, Y. 1984. Effects of glyphosate on caffeic acid metabolism in Perilla cell suspension cultures. Plant Cell Physiol. 25: 185–189.

(5) Lee, T. T. 1980, Characteristics of glyphosate inhibition of growth in soybean and tobacco callus cultures. Weed Res. 20: 365–369.

(6) Lee, T. T. 1982. Mode of action of glyphosate in relation to metabolism of indole-3-acetic acid. Physiol. Plant 54: 289–294.

(7) Lee, T. T. 1982. Promotion of indole-3-acetic acid oxidation by glyphosate in tobacco callus tissue. J. Plant Growth Regul. 1: 37–48.

(8) Lee, T. T. 1984. Release of lateral buds from apical dominance by glyphosate in soybean and pea seedlings. J. Plant Growth Regul. 3: 227–235.

(9) Lee, T. T. and Starratt, A. N. 1986. Inhibition of conjugation of IAA with amino acids by 2,6-dihydroxyacetophenone in *Teucrium canadense*. Phytochemistry 25: 2457–2461.

(10) Lee, T. T., Starratt, A. N. and Jevnikar, J. J. 1982. Regulation of enzymic oxidation of indole-3-acetic acid by phenols: structure-activity relationships. Phytochemistry 21: 517–523.

(11) Steinrucken, H. C. and Amrhein, N. 1980. The herbicide glyphosate is a potent inhibitor of 5-enolpyruvylshikimic acid-3-phosphate synthase. Biochem. Biophys. Res. Commun. 94: 1207–1212.

We claim:

1. A method of protecting desired crop plants from the effect of the herbicide glyphosate comprising applying prior to the application of the herbicide a safening amount of a phenolic compound having an antidotal effect against said herbicide, wherein said phenolic compound is of the formula

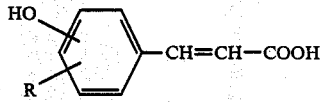

wherein R=H, OH or OCH₃.

2. The method of claim 1 wherein the application and assimilation of the phenolic safener can be achieved by at least one of
   (a) seed treatment before germination,
   (b) localized soil treatment, and
   (c) crop plant or seedling treatment.

3. The method of claim 2 wherein the application of the phenolic safener is to the crop plant, by spraying, 1–2 days in advance of the application of the herbicide glyphosate.

4. The method of claim 2 wherein the application of the phenolic safener is as a localized soil treatment 1–3 days in advance of the application of the herbicide glyphosate.

5. The method of claim 2 wherein the application of the phenolic safener is to the crop plant, by spraying, and as a localized soil treatment 2–3 days in advance of the application of the herbicide glyphosate.

6. The method of claim 1 wherein the phenolic safener is selected from the group consisting of: p-coumaric acid, caffeic acid, ferulic acid.

7. A spray or dusting composition comprising a carrier suitable for plant sprays or dusts and a phenolic compound, selected to have a protective effect against the herbicide glyphosate, said compound having the formula:

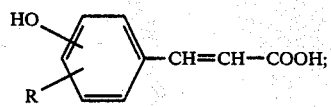

where R=H, OH or OCH₃.

8. The spray or dusting composition of claim 7 where the compound is selected from the group consisting of: p-coumaric acid, caffeic acid, ferulic acid.

* * * * *